(12) United States Patent
Cui

(10) Patent No.: US 11,599,994 B2
(45) Date of Patent: Mar. 7, 2023

(54) SYSTEM AND METHODS FOR CLEAR OPTIMALLY MATCHED PANORAMIC CHANNEL TECHNIQUE FOR DEEP BRAIN PHOTONIC INTERFACE

(71) Applicant: Purdue Research Foundation, West Lafayette, IN (US)

(72) Inventor: Meng Cui, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 469 days.

(21) Appl. No.: 16/833,550

(22) Filed: Mar. 28, 2020

(65) Prior Publication Data

US 2020/0311930 A1 Oct. 1, 2020

Related U.S. Application Data

(60) Provisional application No. 62/825,753, filed on Mar. 28, 2019.

(51) Int. Cl.
| | |
|---|---|
| *G06T 7/00* | (2017.01) |
| *G02B 5/04* | (2006.01) |
| *G02B 13/00* | (2006.01) |
| *H01J 43/28* | (2006.01) |
| *G02B 3/00* | (2006.01) |

(52) U.S. Cl.
CPC .......... *G06T 7/0012* (2013.01); *G02B 3/0087* (2013.01); *G02B 5/04* (2013.01); *G02B 13/0095* (2013.01); *H01J 43/28* (2013.01); *G06T 2207/30016* (2013.01)

(58) Field of Classification Search
CPC ........ G06T 7/0012; G06T 2207/30016; G02B 3/0087; G02B 5/04; G02B 13/0095; G02B 21/0036; G02B 21/0076; H01J 43/28; A61B 5/0042; A61B 5/0071; A61B 5/6852; A61B 5/6868; A61B 2576/026
USPC ........................................................ 382/128
See application file for complete search history.

(56) References Cited

U.S. PATENT DOCUMENTS

| | | | |
|---|---|---|---|
| 6,719,700 B1 * | 4/2004 | Willis | A61B 8/4245 600/462 |
| 2004/0267335 A1 * | 12/2004 | Tulip | A61N 5/062 607/89 |
| 2005/0205667 A1 * | 9/2005 | Rowe | B60R 25/255 235/382 |
| 2005/0228291 A1 * | 10/2005 | Chance | A61B 5/0042 600/407 |
| 2007/0016072 A1 * | 1/2007 | Grunwald | A61B 5/02 600/468 |

(Continued)

OTHER PUBLICATIONS

Chen, T., et al., "Ultrasensitive fluorescent proteins for imaging neuronal activity", Nature, 2013, 499, pp. 295-300.

(Continued)

*Primary Examiner* — Mohammed A Hasan
(74) *Attorney, Agent, or Firm* — Purdue Research Foundation

(57) ABSTRACT

An optical tissue imaging system includes a probe for insertion into a transparent cylindrical capillary. The capillary includes an internal cylindrical channel that extends along a central axis. The capillary is inserted into tissue of a subject, and the probe may rotate and translate within the capillary. The probe may include a mirror configured to reflect light to the tissue outside of the cylindrical capillary.

20 Claims, 10 Drawing Sheets

(56) References Cited

U.S. PATENT DOCUMENTS

| | | | |
|---|---|---|---|
| 2008/0097476 A1* | 4/2008 | Peh | A61B 1/00085 606/130 |
| 2009/0062790 A1* | 3/2009 | Malchano | A61B 18/1492 606/41 |

OTHER PUBLICATIONS

Denk, W., et al., "Photon upmanship: Why multiphoton imaging is more than a gimmick", Neuron, 1997,18, pp. 351-357.

Betley, J., et al., "Neurons for hunger and thirst transmit a negative-valence teaching signal", Nature, 2015, 521, pp. 21.

Cox, J., et al, "Calcium imaging of sleep-wake related neuronal activity in the dorsal pons", Nature communications, 2016, 7, 10763, pp. 7.

Da Silva, J., et al, "Dopamine neuron activity before action initiation gates and invigorates future movements", Nature, 2018, 554, pp. 244-247.

Attardo A., et al, "Impermanence of dendritic spines in live adult CA1 hippocampus", Nature, 2015, 592, pp. 592-596.

Hunnicutt, B., et al., "A comprehensive excitatory input map of the striatum reveals novel functional organization", Elife, 2016, 5, e19103, pp. 32.

Howe, M., et al., "Rapid signalling in distinct dopaminergic axons during locomotion and reward", Nature, 2016, 535, pp. 505-507.

Mittman, W. et al. "Two-photon calcium imaging of evoked activity from L5 somatosensory neurons in vivo", Nature Neuroscience, 2011,14, 8, pp. 1089-1093.

Ouzounov, D., et al. "In vivo three-photon imaging of activity of GCaMP6-labeled neurons deep in intact mouse brain", Nature Methods, 2017,14, 4, pp. 388-390.

Yacoub, E., et al., "High-field fMRI unveils orientation columns in humans", Proceedings of the National Academy of Sciences, 2008,105, 30, pp. 10607-10612.

Levene, M., et al al, "In vivo multiphoton microscopy of deep brain tissue", Journal of neurophysiology, 2004, 91, pp. 1908-1912.

Gobel, W., et al., "Miniaturized two-photon microscope based on a flexible coherent fiber bundle and a gradient-index lens objective" Optics letters, 2004, 29, 21, pp. 2521-2523.

Jung, J., et al., "In vivo mammalian brain imaging using one-and two-photon fluorescence microendoscopy", Journal of neurophysiology, 2004, 92, pp. 3121-3133.

Fu, L., et al., "Characterization of gradient-index lens-fiber spacing toward applications in twophoton fluorescence endoscopy", 2005, Applied optics 44, pp. 7270-7274.

Flusberg, B., et al., "High-speed, miniaturized fluorescence microscopy in freely moving mice", Nature methods, 2008, 5, pp. 935-938.

Chia, T., et al., "Microprisms for in vivo multilayer cortical imaging", Journal of neurophysiology, 2009, 102, pp. 1310-1314.

Bocarsly, M., et al., "Minimally invasive microendoscopy system for in vivo functional imaging of deep nuclei in the mouse brain", Biomedical optics express, 2015, 6, pp. 4546-4556.

Barreto, R., et al, "Time-lapse imaging of disease progression in deep brain areas using fluorescence microendoscopy", Nature medicine, 2011, 17, pp. 223-228.

Yang, W., et al., "In vivo imaging of neural activity", Nature methods, 2017, 14, pp. 349-359.

Tearney, G., et al, "In vivo endoscopic optical biopsy with optical coherence tomography", 1997, Science 276, pp. 2037-2039.

Kim, P., et al., "In vivo wide-area cellular imaging by side-view endomicroscopy", Nature methods, 2010, 7, pp. 303-305.

Leith, E., et al., "Reconstructed wavefronts and communication theory", JOSA, 1962, 52, pp. 1123-1130.

Tang, J., et al., "Superpenetration optical microscopy by iterative multiphoton adaptive compensation technique", Proceedings of the National Academy of Sciences of the United States of America, 2012, 109, pp. 8434-8439.

Sych, Y., et al., "High-density multi-fiber photometry for studying large-scale brain circuit dynamics", Nature methods 2019, 16, pp. 553-560.

Guo, Q. et al., "Multi-channel fiber photometry for population neuronal activity recording", Biomedical optics express, 2015, 6, pp. 3919-3931.

Lu, L. et al., "Wireless optoelectronic photometers for monitoring neuronal dynamics in the deep brain", Proceedings of the National Academy of Sciences, 2018,115, pp. E1374-E1383.

Gunaydin, L.A. et al., "Natural neural projection dynamics underlying social behavior", Cell, 2014, 157, pp. 1535-1551.

Eban-Rothschild, A., et al., "VTA dopaminergic neurons regulate ethologically relevant sleep-wake behaviors", Nature neuroscience, 2016, 19, pp. 1356-1366.

Garfield, A., et al., "Dynamic GABAergic afferent modulation of AgRP neurons", Nature neuroscience, 2016, 19, pp. 1628-1635.

Cho, J., et al., "Dorsal raphe dopamine neurons modulate arousal and promote wakefulness by salient stimuli". Neuron, 2017, 94, pp. 1205-1219.

\* cited by examiner

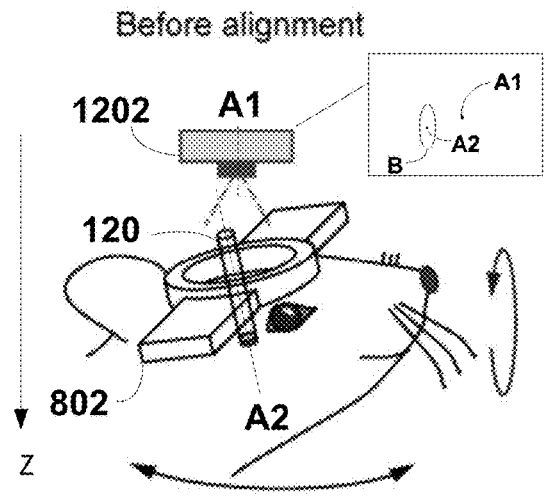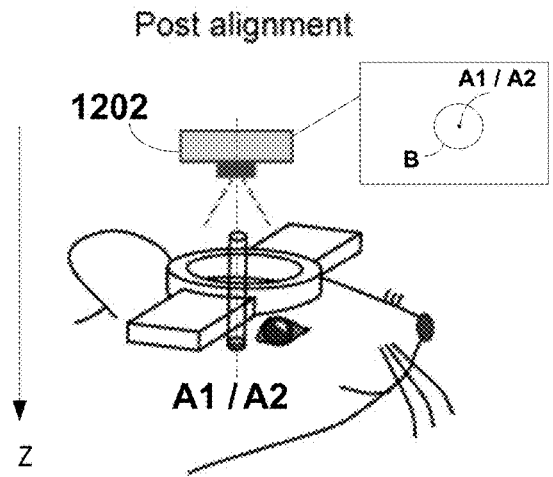
FIG. 12A  FIG. 12B
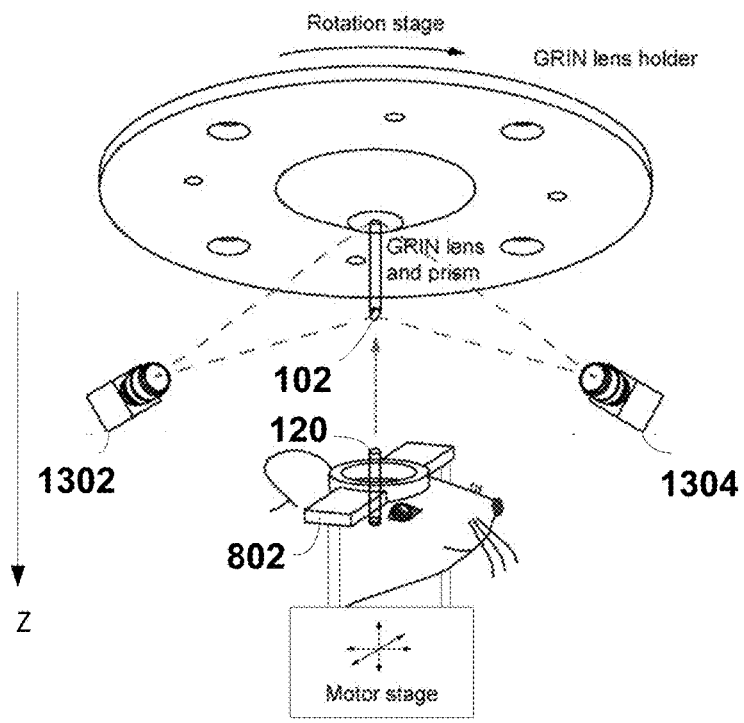
FIG. 13

SYSTEM AND METHODS FOR CLEAR OPTIMALLY MATCHED PANORAMIC CHANNEL TECHNIQUE FOR DEEP BRAIN PHOTONIC INTERFACE

CROSS-REFERENCE TO RELATED APPLICATIONS

This application claims the benefit of U.S. Provisional Application No. 62/825,753 filed Mar. 28, 2019 which is hereby incorporated by reference in its entirety.

GOVERNMENT RIGHTS

This invention was made with government support under NS107689 awarded by the National Institutes of Health. The government has certain rights in the invention.

TECHNICAL FIELD

The present disclosure relates to in vivo imaging of tissue, and more specifically to neural tissue imaging.

BACKGROUND

In vivo cellular resolution function (e.g. calcium) imaging and (e.g. optogenetics) has revolutionized examination of neuronal networks. Neurophotonics has emerged as an important tool for study and interface with the brain. Despite these advances, present approaches to deep tissue access leaves much of the subject's brain region inaccessible. A major limitation of neurophotonics is the tissue access depth. Due to the spatially and temporally random light scattering, cellular resolution optical access has been fundamentally limited to ~1 mm in mammalian brain tissue even with the help of multiphoton excitation, leaving large portions of brain regions inaccessible. Miniature optical components provide access to greater depths, but traditional approaches still provide limited viewing. In many traditional approaches, the viewable region is provided at the tip of the inserted device (akin viewing through a tunnel) leaving a large portion of the accessed tissue unviewable.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

FIGS. 12A-B illustrates an example of a capillary alignment camera;

FIG. 13 illustrates an example of probe alignment cameras;

DETAILED DESCRIPTION

Figure 1:
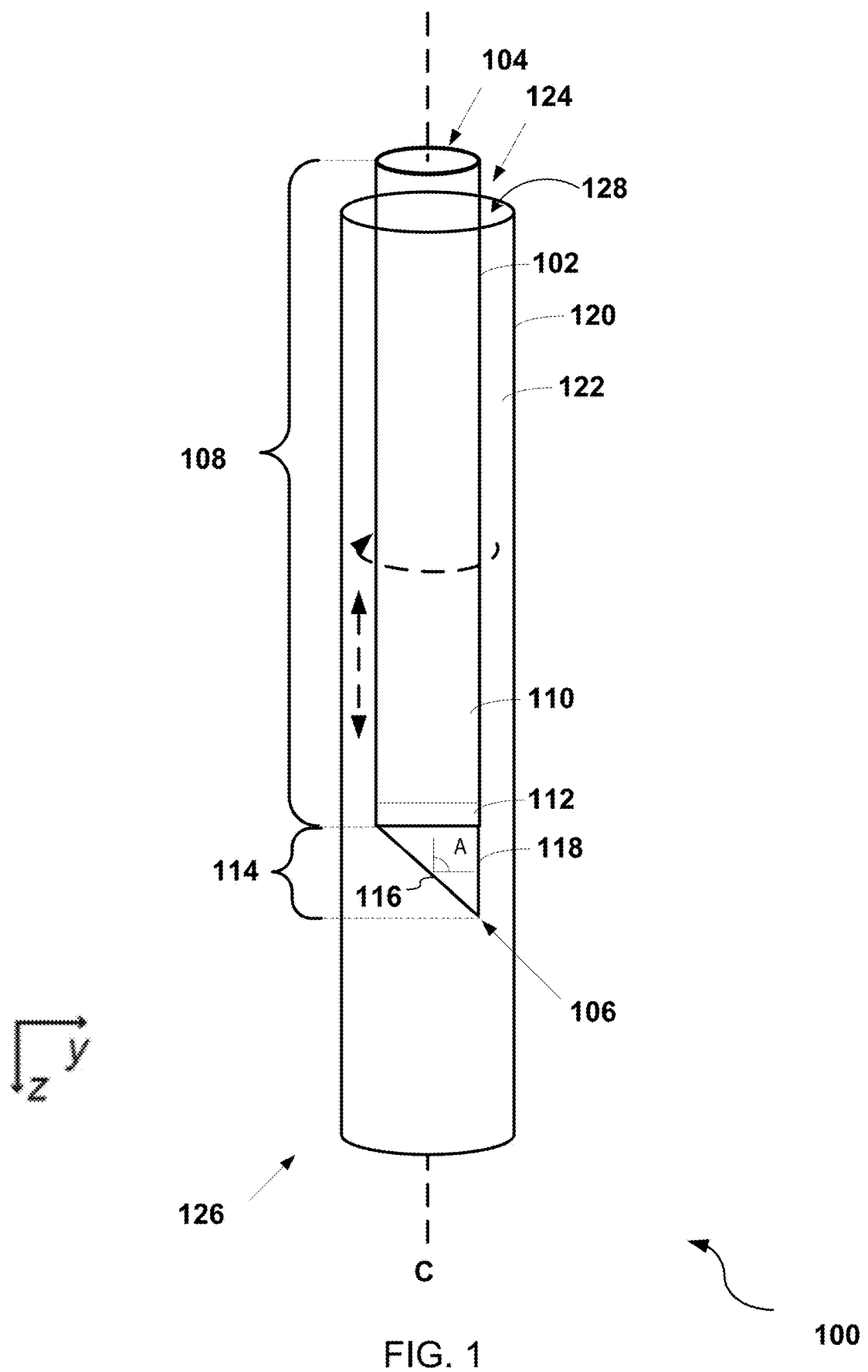
FIG. 1 illustrates a first example of an optical tissue imaging system.

Due to the spatially and temporally random light scattering, cellular resolution optical access has been fundamentally limited to ~1 mm in mammalian brain tissue even with the help of multiphoton excitation, which is about the thickness of a mouse brain neocortex. To access deep brain regions, the method of choice is to insert miniature optical components. However, traditional devices have a very limited access with respect to tissue volume, providing only a tiny fraction of the volume of the inserted optical element. Geometrically, the viewable region is only at the tip of the inserted device, akin viewing through a tunnel.

Accordingly, there is disclosed system, device, and methods for Tissue Imaging are provided. By way of introductory example, an optical tissue imaging system may include a transparent cylindrical capillary for insertion into brain tissue. The capillary may have an internal cylindrical channel that extends along a central axis of the capillary. The system may further include an optical prob. The probe may include a mirror configured to reflect light to the tissue adjacent to a cylindrical wall of the cylindrical capillary. The probe may be rotatable within the capillary and movable along the central axis of the capillary.

The system and methods described herein provide various technical advancements. For example, the system may enable a clear optically matched panoramic access channel technique (COMPACT), which drastically overcomes the tissue access volume constraint. With the same insertion device volume, the system may provide two to three (or more) orders of magnitude increase in tissue access volume. For example, the system may enable a 360-degree panoramic view around the inserted probe throughout the entire insertion length. Thus unlike convention approaches of directly inserting probe inside brain tissue, the system may insert a probe inside of channel embedded in tissue. The probe may freely move within the channel to maximize imaging area. The translation of the probe along the channel allows us to image through the entire insertion length.

In some examples, the capillary may be filled with a fluid, which isolates the probe from the tissue and provides refractive index matching with the tissue. While the fluid provides refractive index matching, it may also contribute to mechanical coupling during high-speed rotation and/or translation and generally result in a slower imaging process. To address these technical concerns, the probe may include an aspherical mirror to account for the refractive index matching of the tissue. With the aspherical reflection surface, air may be used instead of fluid to separate the capillary from the probe. Using air may minimize disturbances cause by high-speed probe rotation/translation and generally result in faster imaging times.

Additional and alternative benefits, efficiencies, and improvements over existing market solutions are made evident in the systems and methods described below.

FIG. 1 illustrates a first example of an optical tissue imaging system 100. The optical tissue imaging system 100 may include a probe 102. The probe 102 may include a narrow tube, elongated along a central axis C. The probe 102 may include a proximal end 104 and a distal end 106. The proximal end may be attached to a mechanical device which rotates, translates, and/or emits excitation light and/or receives emitted or reflected light. The distal end 106 may include an end inserted into a subject for imaging.

The probe 102 may include a lens configuration 108 and a mirror 116. The lens configuration 108 may include one or more lenses that direct emission light onto a mirror 116. The lens configuration 108 may include a relay lens 110, a micro objective lens 112, or a combination thereof. In some examples, a gradient index (GRIN) lens can be used as the relay lens. For example, the GRIN lens may achieve function of both the relay lens and the micro objective lens. The relay 110 may deliver the light in and out of the probe 102 and serve as a relay lens. The micro objective lens 112 may provide a sharp focus for imaging. In other examples, the probe may include the relay lens 110 without the micro objective lens. For example, the relay lens 110 may serve the purpose of both relay lens and the micro objective lens configuration 108

The mirror 116 may include a surface that redirects light at an angle A, such as 90 degrees or some other specified angle, with respect to the central axes C of the probe 102 and/or the capillary 120. In some example, the mirror 116 may include (or be included in) a folding mirror or a prism. For example, the mirror may be angled between 30 and 150 degrees relative to the central axis C. Thus, when light is sent down the probe 102 along the central axis C and through the lens configuration 108, the mirror 116 may reflect the light at an angle and onto tissue that is external to the probe 102. The mirror 116 may reflect light from to the tissue back through the probe 102. Thus, when the probe is viewed down the central access C in the Z direction, the mirror 116 may provide a view of tissue circumferential to the capillary 120.

The probe 102 may include a head 114. The head 114 may include a portion of the probe 102 at the distal end of the probe 102. For example, the head 114 may include a folding mirror, a prism, or, more, generally, a mirror. Alternatively or in addition, the probe head may include components that hold the mirror.

For example, the head 114 of the probe 102 may include a one or more wall 118. The wall 118 may include a structure coupled to the mirror 116 or included with the mirror 116. The wall 118 may be transparent and permit light to travel to and from the mirror 116. As illustrated in FIG. 1, the wall 118 may bond to the lens configuration 108. For example, the wall 118 may bond to the micro-objective lens 112. In other examples (i.e. examples without the micro objective lens 112), the wall 118 may bond directly to the relay lens. Other configurations are possible than those illustrated in FIG. 1 (e.g. see FIGS. 4-6).

The system may include a capillary 120. The capillary 120 may include a transparent tube that is inserted into tissue to be studied or examined. For example, the capillary may include a cylindrical wall that defines an internal channel 122. In some examples, the capillary 120 may include an ultrathin quartz cylindrical wall and/or fused silica (see FIGS. 2-3 for examples of dimensions). The cylindrical wall may extend along a central axis C. The capillary 120 may include a proximal end 124 and a distal end 126 opposite the proximal end 124. The distal end 126 may be inserted into tissue. The distal end 126 may be sealed (closed end). The proximal end 124 may include an opening 128 for the internal cavity 120. The opening 128 may receive the probe 102.

To perform panoramic imaging, the probe 102 may rotate within the capillary channel 122. For example, the optics probe 102 may spin within the capillary channel 122. Alternatively or in addition, the optics probe 102 may translate back and forth along the channel 122 in a direction substantially parallel to the central axis C of the capillary 120. By translating and/or rotating the probe 102 along the channel 122, the length of the tissue surrounding may be imaged at various depths in a panoramic manner.

In some examples, the channel 122 may be filled with a liquid fluid (e.g. water) whose refractive index matches that of the surrounding biological tissue. The index matching may eliminate the aberration which would otherwise distort imaging due to the curved capillary channel surface and the refractive index mismatch between air inside and the tissue outside. Alternatively, the mirror 116 may include an aspherical reflection surface (See FIGS. 5-6), which allows air to be present inside the capillary channel 122 instead of fluid.

Figure 2:
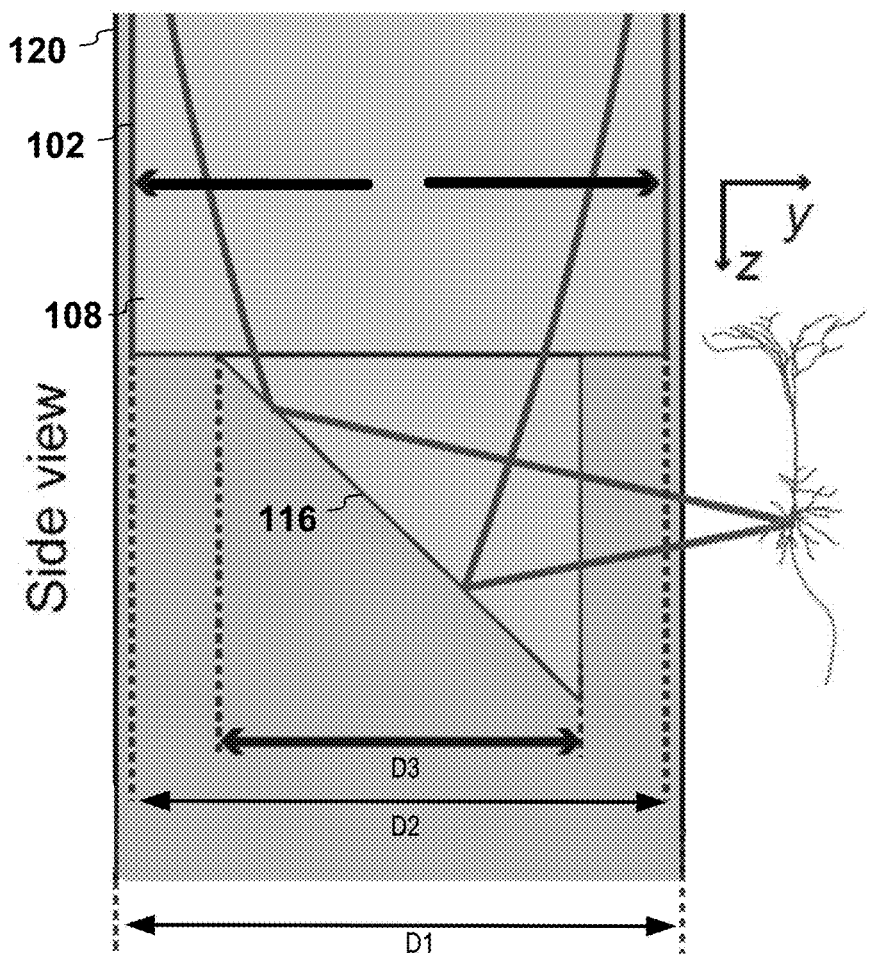
FIG. 2 illustrates a side view of a capillary and a probe.
Figure 3:
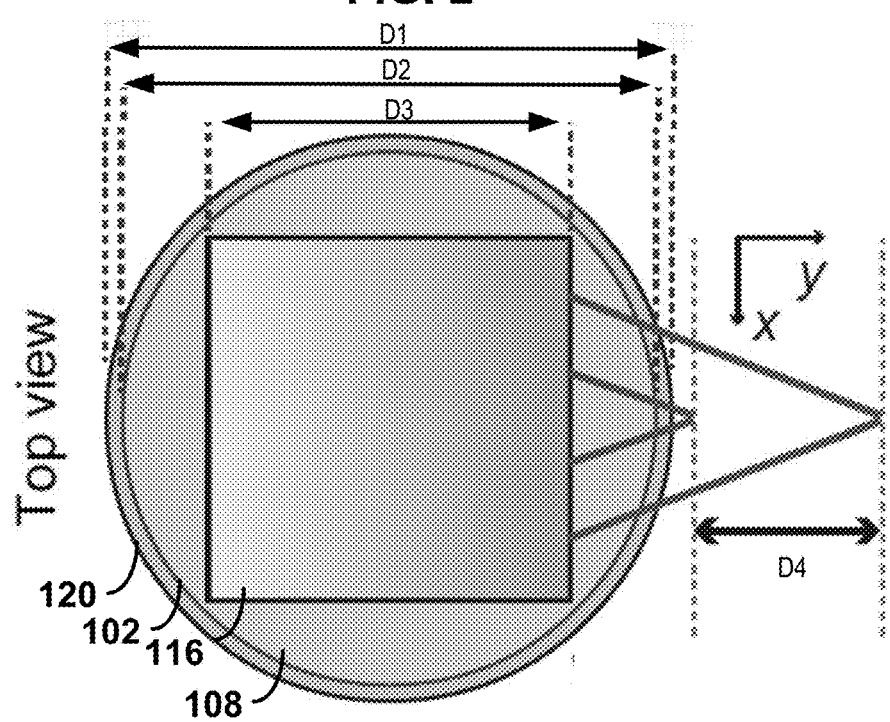
FIG. 3 illustrates a top view of an capillary and a probe.

FIG. 2 illustrates a side view of the capillary 120 and probe 102. FIG. 3 illustrates a top view of the capillary 120 and probe 102. Referring to FIGS. 2 and 3, the capillary 120 may have a diameter (D1) in a range of 0.1-5 mm. The capillary wall may have a thickness of 0.01-0.1 mm. The lens configuration 108 of the probe 102 may have a diameter (D2) of 0.1-5 mm. The mirror 116 may have a width (D3) of 0.07-3.5 mm. The probe 102 may provide a workable viewing distance (D4) between 0 and 1000 μm. In various examples, the excitation numerical aperture (NA) for imaging 0-1000 μm outside the prism facet may range between 0.3-0.8 while the signal collection NA may be 0.4-0.85, though these values may vary depending on the implementation and quality of components. It is interesting to note that just slight rotation (120 degree) can yield very wide FOV. For example, spinning a 1 mm diameter probe over 360 degrees while imaging ~300 μm outside the channel 122 can yielded a ~5 mm wide panoramic view.

Figure 4:
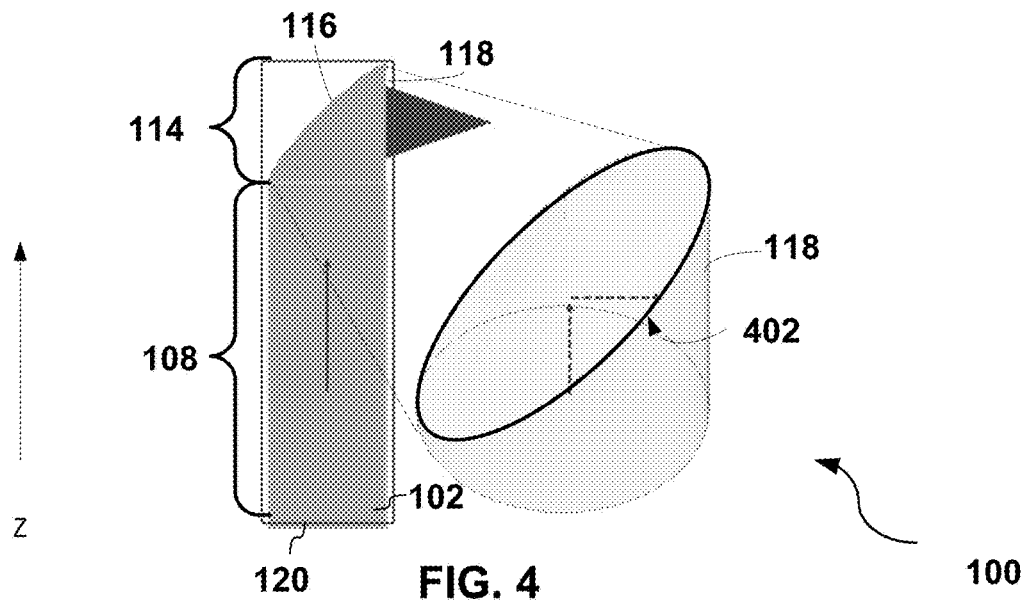
FIG. 4 illustrates a second example of an optical tissue imaging system.

FIG. 4 illustrates a second example of the optical tissue imaging system 100. In some examples, the mirror 116 may include an aspherical reflection surface 402. The aspherical reflection surface 402 may be concave with respect to the optical path. The lens configuration 108 may deliver excitation laser light to the aspherical reflection surface 402. The reflected or emitted light will then travel through a transparent wall 118 of the probe head 114, an air gap between the probe 102 and the capillary 120, the capillary 120, and enter biological tissue. Light reflected/emitted from the tissue will travel this path in reverse order. The optical aberration encountered by the light through this path will be fully compensated by the aspherical reflection surface 402. The surface 402 may be fabricated by high resolution 3D printing followed by an optical reflection coating on the aspherical surface or by diamond milling. For imaging, the probe 102 may be spun and translated such that the optical focus will travel through the surrounding biological tissue. Without fluid in the capillary 120, operational mechanical disturbances of the surrounding tissue are limited during high-speed movement of the probe 102.

Figure 5:
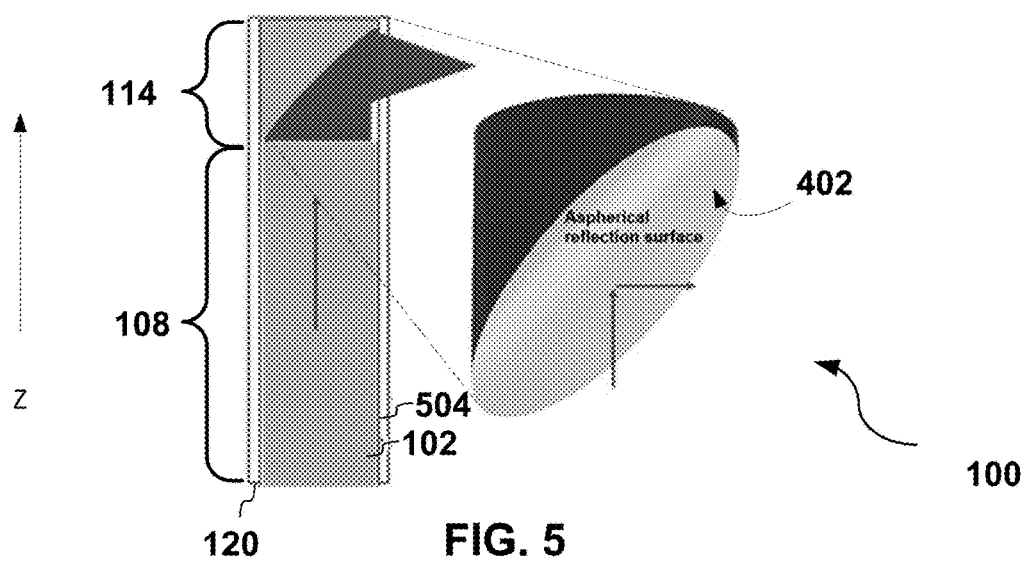
FIG. 5 illustrates a third example of an optical tissue imaging system.

FIG. 5 illustrates a third example of the optical tissue imaging system 100. The probe 102 may include an inner capillary 504. The lenses 108 and/or the probe head 114 may be disposed in the inner capillary 504. For example, the mirror 116 may disposed in the inner capillary 504. The inner capillary 504, along with the lens configuration 108 and the mirror 116, may rotate and/or translate in an outer cavity 120.

An advantage of the inner cavity 504 is that the probe head 114 may be oriented in various configurations that require minimal or no bonding with the lens configuration 108. By way of example, the probe head 114 may bond to the inner capillary instead of the lens configuration 108.

In the example illustrated in FIG. 5, and related examples, excitation light may travel through the lens configuration 108, onto aspherical reflection surface 402, through the inner and outer lenses capillaries, and onto the tissue surrounding the outer capillary 120. The optical aberration encountered in the path will be compensated by the aspherical reflection surface 402. In some examples, the aspherical reflect surface may be fabricated by high precision 3D printing followed by metal coating on the surface, or by direct diamond milling. For imaging, the probe 102 may be spun and translated. In response to spinning and/or translating, the laser focus will be scanned over the biological tissue volume around the outer capillary.

Figure 6:
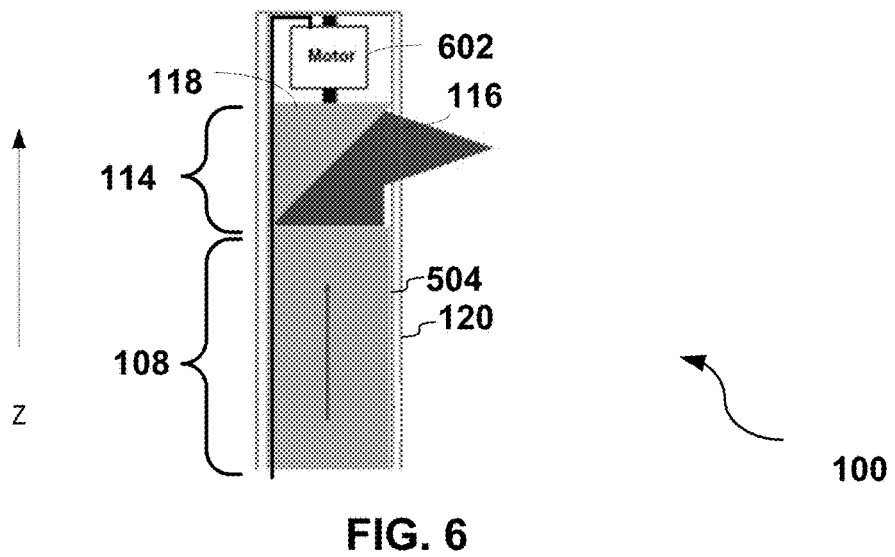
FIG. 6 illustrates a fifth example of an optical tissue imaging system.

FIG. 6 illustrates a fourth example of the optical tissue imaging system 100. In some examples, probe head 114 may spin independent of the lens configuration 108. For example, the probe 102 may include a micromotor 602. The probe head 114 bond to the micromotor 602. The micromotor 602 may bond to the inner capillary wall 118 and/or the mirror 116. The motor 602 may spin the probe head 114 to cause the mirror 116 to rotate within the inner capillary and independent of the lens configuration 108. The inner capillary may translate in the outer cavity to vary the imaging depth and the micromotor 602 rotates the mirror 116 to perform panoramic scanning.

Figure 7:
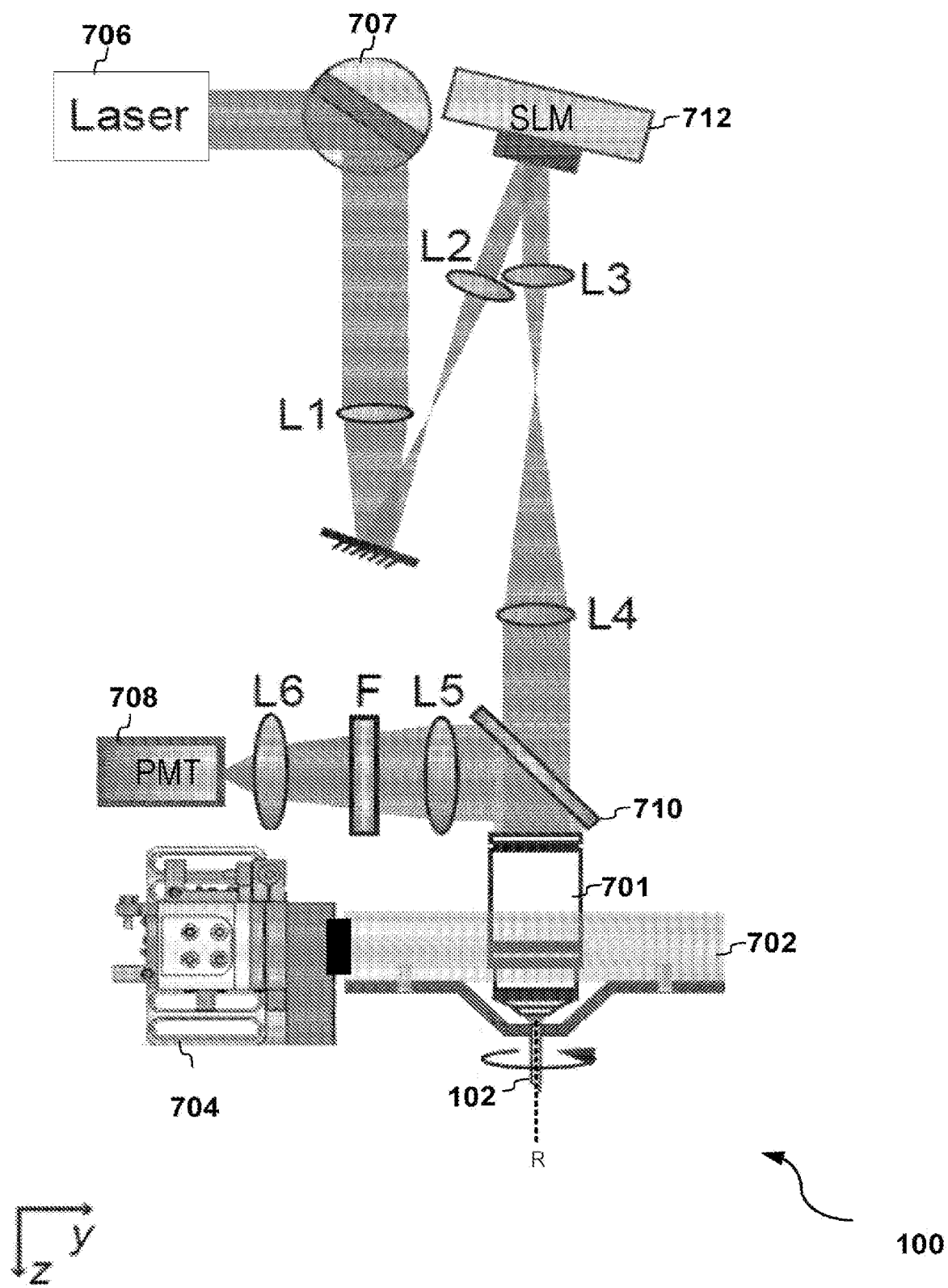
FIG. 7 illustrates a sixth example of an optical tissue imaging system.

FIG. 7 illustrates a sixth example of the optical tissue imaging system 100. The system 100 may be configured for fixed-head two-photon imaging (as illustrated in FIG. 7). The components (or a portion thereof) may be arranged for mobile imaging, one photon imaging, and/or photometry.

The system 100 may include an objective lens 701 external to the probe 102. The external objective lens 701 may direct light in or out of the probe. The external objective lens may include for example, an OLYMPUS 20× NA 0.5, ZEISS 20× NA 0.75, or some other suitable lens.

The system 100 may include a rotary stage 702. The rotary stage 702 may rotate the probe 102. For example, the rotary stage 702 may include motor that spins about the rotational axis R. Alternatively or in addition, the rotary stage 702 may include a base, a platform, and/or bearings. The probe 102 may attach to the platform and rotate about the rotation axis R.

The system 100 may include a translation stage 704. The translation stage 704 may cause the probe 102 and/or the rotary stage to translate in a direction along the rotational axis R. For example, the translation stage may include a three-axis linear translation stage. The translation stage 704 for couple to the rotary stage 702 to cause translation of the rotary stage in the z direction. In other examples, a separate motorized stage may connect to the subject to cause translation of the subject and insertion of the probe 102 into the capillary (e.g., capillary 120).

The system 100 may include a light source 706. The light source 706 may include a light emitter, such as a laser, that is directed to the probe 102 and ultimately onto the examined tissue. For example, the light source 706 may include an electrically powered light source, such as a light emitting diode (LED) or other light source capable of producing illuminating light. For example, the light source may include a laser, LED, and/or a lamp. Alternatively, the light source 706 may include an optical source, such as optical fiber, where the light is generated external to the system and/or transferred to the system via optical fiber or the like.

The system 100 may include a scanning mirror 707. For example, the scanning mirror 707 may include, for example, a two-axis Galvo scanning mirror, which scans the laser beam in a direction transverse to a direction of emission.

The system 100 may include a light sensor 708. The light sensor 708 may include a sensor that generates a measurement of light and/or color intensity. For example, the light sensor 708 may receive laser-excited fluorescent light reflected from tissue and generate intensity measurement information corresponding to the fluorescent light. In two photon imaging, the light sensor 708 may include a photomultiplier tube (PMT), as illustrated in FIG. 7. For two photon imaging, the detection is done with a PMT that collects all the emitted fluorescence. For one photon imaging, the light sensor 708 may include a CCD or CMOS sensor. Alternatively or in addition, the light sensor 708 may include (or may be included in) a camera, such as a digital camera, which renders images of tissue surrounding and adjacent to the probe 102. For example, the camera may receive the reflected light from the mirror and generate wide field images of the tissue surrounding the capillary as the probe is rotated and moved along the axis of the capillary.

The system 100 may include a beam splitter 710. The beam splitter 710 may include an optical device that splits a beam of light. In some examples, the beam splitter 710 may include a dichroic beam splitter, and direct fluorescence emission received from the probe 102 to the light sensor 708. In other words, the beam splitter 710 may detect and split fluorescence emission, which differs from the excitation light in wavelength.

The system 100 may include a special light modulator (SLM) 712. The SLM 712 may compensate the aberration in the relay lens 110 (FIG. 1) to provide increased image quality. In various experimentations, it was found that a 15 µm thin capillary wall induced insignificant aberration for two-photon excitation with NA≤0.5. However, the SLM 212 may compensate the overall system aberration in imaging path. Light from the SLM may be imaged onto the back focal plane of the lens configuration 108 for the probe 102.

The system may include a mirror M1, optical lenses L1-6 and/or optical filter(s) F. The arrangement and inclusion of the mirrors, optical lens(es), and or optical filter(s) may vary depending the imaging type.

In some examples, the system 100 operate without the rotary stage 702 and/or the translation stage 704. For example, an O-ring may be placed on the probe, and the probe may be dropped inside the capillary (e.g., capillary 120). The depth probe inside the capillary (e.g., capillary 120) may be varied by adjusting the O-ring position. The rotation of the probe 102 may be manually controlled.

During experimentation of the system and methods described herein, imaging was performed on mice brains at various depths and regions. The system provided the freedom to visit a large volume of brain tissue. For the experiments, a probe insertion range and spinning range of interest was established. The probe 102 was calibrated to visit the defined location in sequence. At each location, the SLM driven defocusing synchronously coordinated with the galvo scanning to record 3D image stacks.

Even with the moderate NA employed in experimentation, fine neuronal structures, such as axonal boutons, were observed. To evaluate the system's performance for in vivo calcium imaging, the subjects were imaged expressing neurons in the brain of awake mice. Following a virus injection, the capillary was surgically inserted. Four weeks after the surgery, in vivo imaging was carried out in head-fixed awake mice. Spontaneous calcium transients deep in hippocampus were recorded with the two-photon based high contrast imaging. It is worth noting that the system may handle substantial tissue motion during awake animal calcium recording. The probe flexibly moved with the quartz capillary to tolerate significant tissue movement. These imaging results from awake mice indicate that the system was compatible with in vivo calcium signal recording.

Compared to established miniature probe for deep brain calcium recording, the system 100 has its key advantages in its massive tissue access volume and adaptability. For example conventional approaches typically deliver a ~0.2 mm diameter two photon imaging FOV and can image ~0.3 mm outside the system, yielding a tissue access volume of 0.009 $mm^3$. The system described herein of the same insertion diameter may allow a circular imaging FOV of ~5 mm or better. Assuming that the translation along the capillary is 3 mm, the system offers a tissue access volume of ~4 $mm^3$, which is two to three orders of magnitude greater than that of the conventional method.

Such a huge increase in access volume provides tremendous flexibility to explore the neurons of interest and therefore greatly increase the success rate of finding neurons relevant for the studies and the overall experiment throughput. In principle, we also have the freedom to switch the probe 102 to visit the same population of neurons. For example, we could switch between probes of different NA for the tradeoff between simultaneous imaging FOV and spatial resolution, similar to switching objective lens under a conventional microscope, or switch between one photon wide field recording and two-photon imaging for tradeoff between imaging throughput and imaging depth.

Figures 8, 9:
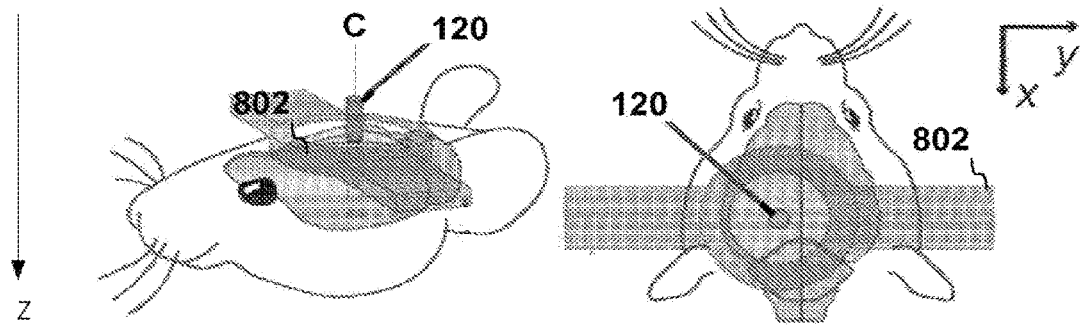
FIG. 8 illustrates a perspective view of a headbar.
FIG. 9 illustrates a top view of a headbar.

FIG. 8 illustrates a perspective view of a headbar 802. FIG. 9 illustrates a top view of the headbar 802. The headbar 802 may be coupled to a mammal's head and manipulated for capillary alignment.

Figure 10:
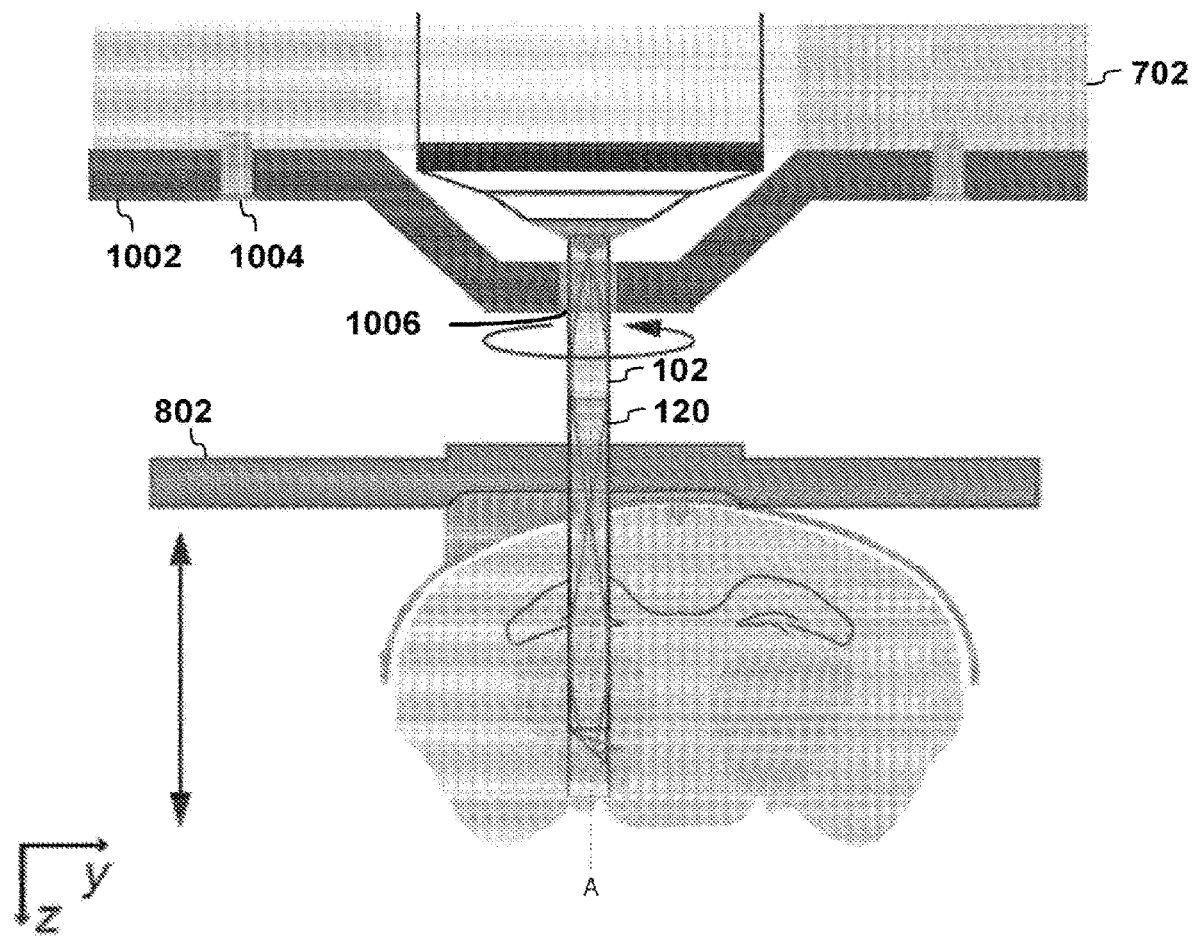
FIG. 10 illustrates a side view of a headbar aligned for probe insertion.

FIG. 10 illustrates a side view of the headbar 802 aligned for probe insertion. As illustrated in FIG. 10, the axis of the probe 102, the axis of the rotary stage, and the axis of the capillary 120 are all substantially aligned along a common axis A.

In some examples, the rotation stage 702 may removably couple to a lens holder 1002. In some examples, the lenses holder 1002 may include a disk that holds the probe 102. The lens holder may removably couple with the rotation stage by way of one or more fasteners 1004.

In some examples, lens holder 1002 may retain the probe 102 by friction. For example, lenses holder may include an O-ring 1006 or other gasket that receives and secures the probe 102.

Figure 11:
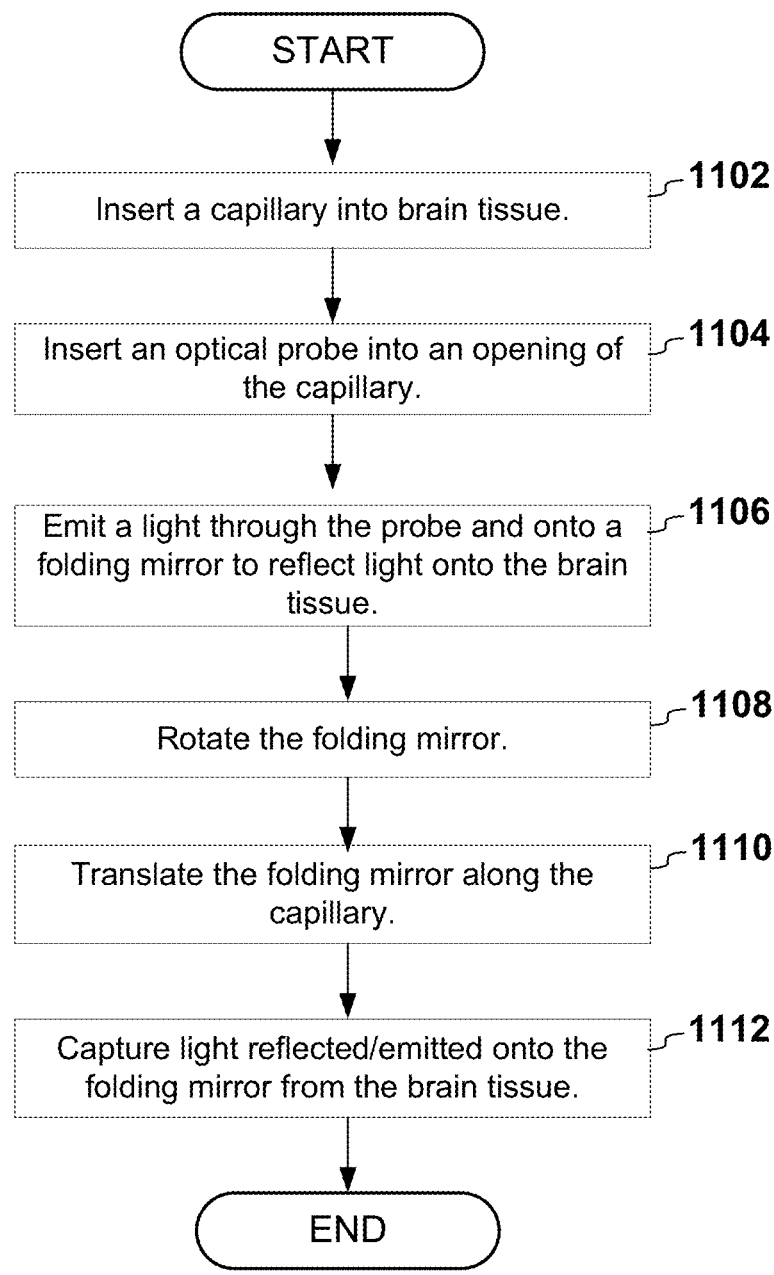
FIG. 11 illustrates a flow diagram of operations of a system.

FIG. 11 illustrates a flow diagram of operations of the system 100. The following discussion referring to FIG. 11, and other descriptions of flow diagrams herein, refer to operations being performed by the system. It should be appreciated that the systems may include one or more hardware processors that cause performance of the operations. Alternatively or in addition, the system may provide one or more user interfaces such as interactive displays, buttons, and/or other analog or digital controls that cause actuation of mechanical devices described herein to perform the operations.

The system may insert the capillary 120 into brain tissue (1102). For example, the capillary 120 may be at least partially disposed into the brain tissue such that the opening of the capillary 120 at the proximal end is exposed.

The system may insert the probe 102 into the opening of the capillary 120 (1104). For example the opening may receive the probe 102. A translation stage may cause the probe to move in a direction along the central axis of the capillary 120. Alternatively or in addition, a translation stage may couple to the mammal and cause the capillary inside the mammal to align with the probe 102.

The system may emit a light through the probe 102 and onto the mirror 116 to reflect light onto the brain tissue (1106). For example, a light source may energize and send light through various components, such as a Galvo scanning mirror, a spatial light modulator, and other components as described in reference to FIG. 7. The light received by the probe 102 may travel through the lens configuration 108 and onto the mirror 116. The mirror 116 may reflect light through the transparent wall of the capillary 120 and onto the tissue adjacent to the capillary 120.

The system may rotate the mirror 116 (1108). For example, the rotation stage may rotate the probe 102, which causes the mirror 116 to rotate within the capillary 120. Thus, the mirror 116 and/or the probe 102 may rotate while the capillary 120 remains stationary. In other examples, the mirror 116 may rotate while other portions of the probe 102 remain stationary. For example, a micromotor 602 may rotate the head 114 of the probe 102 while the lens configuration 108 remains stationary (see FIG. 6).

The system may translate the mirror 116 along the capillary 120 (1110). For example, the translation stage may move the probe 102 along central axis of the capillary 120 at varying various depths. The capillary 120 may remain stationary while the probe 102 moves.

The system may capture light reflected onto the mirror 116 from the brain tissue (1112). The probe 102 may be rotated and/or translated to provide a view to the tissue circumferentially surrounding the capillary 120 at various depths. In response to the probe 102 being translated, the brain may be imaged at various specified depths. In response to the probe 102 being rotated, the brain may be imaged at various specified circumferential locations around the capillary 120.

FIGS. 12A-B and 13 illustrate an example of the system with alignment cameras. For panoramic imaging around the capillary 120, the probe 102 should precisely spin around the rotation axis of the rotary stage. Thus, both the probe 102 and the capillary 120 should be well aligned with respect to the rotation axis. The cameras also guide the process of inserting the probe 102 inside the capillary 120. After the insertion, the optics probe 102 may be rotated for panoramic imaging by controlling the rotary stage.

As illustrated in FIGS. 12A-B, the system may further include a capillary alignment camera 1202. Image data from capillary alignment camera 1202 may be accessed to align the capillary 120 prior to probe insertion. By way of example, the capillary alignment camera 1202 may point in a direction (Z) to provide a line of sight. A subject with an inserted capillary may be positioned such that the capillary 120 is in line of sight of the capillary alignment camera. In other words, the camera may point in the direction z toward the mouse head where the opening of the capillary 120 is exposed. At this point, the capillary 120 is not yet aligned.

The capillary alignment camera may generate image data. The capillary alignment camera may be aligned with a camera axis A1. The location of the camera axis in the image data may be predetermined and/or pre-calibrated. The system may determine the boundaries of the opening of the capillary 120. A translation stage and/or rotary stage attached to the mouse (or the holder 802) may rotate and/or translate the mouse to cause alignment, as illustrated in FIG. 12B. The system may determine whether alignment is achieved based on the dimensions of the detected boundary (i.e. radius, circumference, diameter, etc.), the relative locations of the camera axis A1 and the capillary axis A2, or a combination thereof. For example, the system may include an alignment criterion that compares the circumference, diameter, radius, distance between axis, and/or other measurements to predetermined values.

FIG. 13 illustrates an example of the system with probe alignment cameras 1302-1304. The probe alignment cameras 1302-1304 may point in corresponding directions that intersects the rotational axis of the rotational axis of the rotary stage. In some examples, the probe alignment cameras may each face the rotational axis R, but point in orthogonal or near orthogonal directions (X,Y).

The probe 102 may be attached to the lens holder and/or rotary stage (e.g. see FIG. 10). After attachment, the probe 102 may be positioned in line of sight of the probe alignment cameras 1302-1304. The rotary stage may cause the probe 102 to spin. For example, the rotary stage may be commanded to spin the probe 102 over 360 degrees in 12 steps (although a larger or smaller number of steps may be used). The cameras 1302-1304 may record images of the probe 102 during the rotation. Using image processing, the boundaries of the probe 102 in the various images may be determined. The average location of the edges over the measurements yields the rotational axis R of the rotation stage.

By way of example, the system 100 may identify a plurality of vectors representative of the outer edges of the probe 102 at various times. The system may determine an average vector. The average vector may represent the rotational axis. Once the rotational axis is known, the probe 102 may be moved/adjusted to align the central axis of the probe 102 with the rotational axis.

In some examples, the image data from the probe alignment cameras 1302-1304 may be evaluated to align the capillary 120 with the rotational axis. For example, at least a portion an inserted capillary may be visible after insertion in a subject. After the subject is aligned with capillary alignment camera, the subject may be translated such that the exposed portion of the capillary 120 is in line of sight of the probe alignment capillaries. Based on image data provided by the probe alignment cameras 1302-1304, the central axis of the capillary may be substantially aligned with the rotational axis of the probe 102.

In some examples, the rotational axis determined by the probe alignment cameras 1302-1304 may be used to calibrate the capillary alignment camera. For example, based on image data provided by the capillary alignment camera 1202 (FIG. 12), a non-inserted capillary may be aligned with the rotational axis. The non-inserted capillary may be translated to a position in line of sight of the capillary alignment camera, without changing the angle of the non-inserted capillary with respect to the Z direction. The capillary alignment camera 1202 may be adjusted to align the viewing axis of the camera 1202 with the central axis of the non-inserted capillary. For daily operation, the subject and/or inserted capillary channel is positioned under the calibrated capillary alignment camera 1202. The orientation of the channel is adjusted by, for example, moving the headbar 802 to reposition the subject so that the central axis A1 of the capillary 120 is aligned with imaging axis A2 of capillary alignment camera. After this, the subject is translated to be under the probe 102. Based on imaging data provided by the capillary alignment cameras, the channel is moved that the bottom end of the probe 102 is inserted inside the capillary 120. After this step, we can freely translate the capillary 120 and/or the probe 102 and command the rotation stage to spin the probe 102.

In some examples, the system 100 may include a motor stage. The motor stage may couple to the headbar 802. The motor stage may cause the headbar 802 to translate along the X, Y, and/or Z directions and/or rotate. Thus, the motor stage may translate the subject and/or capillary in line of sight of the probe alignment cameras 1302-1304 and/or the capillary alignment camera 1202 (FIG. 12). It should also be appreciated that in some examples, the motor stage may cause the headbar 802 to translate with respect to the Z direction. For example, the motor stage may cause the headbar 802 to translate such that the capillary 120 receives the probe 102.

Figure 14:
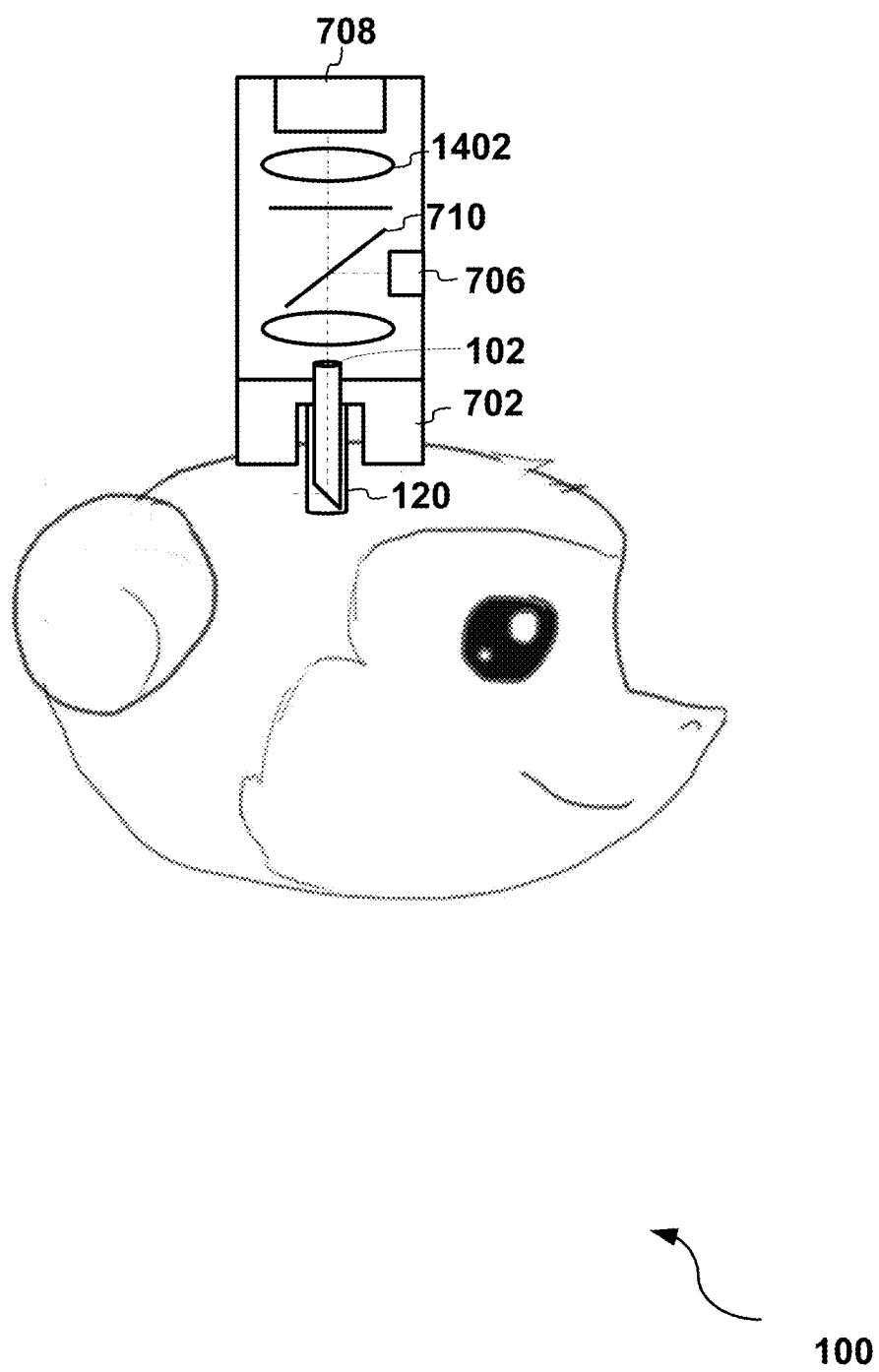
FIG. 14 illustrates a seventh example of an optical tissue imaging system.

FIG. 14 illustrates a seventh example of the system 100. In some examples, the system may be head-mounted on freely-moving animals. The light source may include, for example, a LED inside the enclosure or use optical fiber to couple the light into the enclosure. The beam splitter 710 may direct the illumination light onto the probe. The fluorescence emission may be imaged by lenses onto the light sensor 708 (e.g. a digital camera). The system may include an optical filter 1402 to block the illumination light and only transmit the fluorescence emission.

Figure 15:
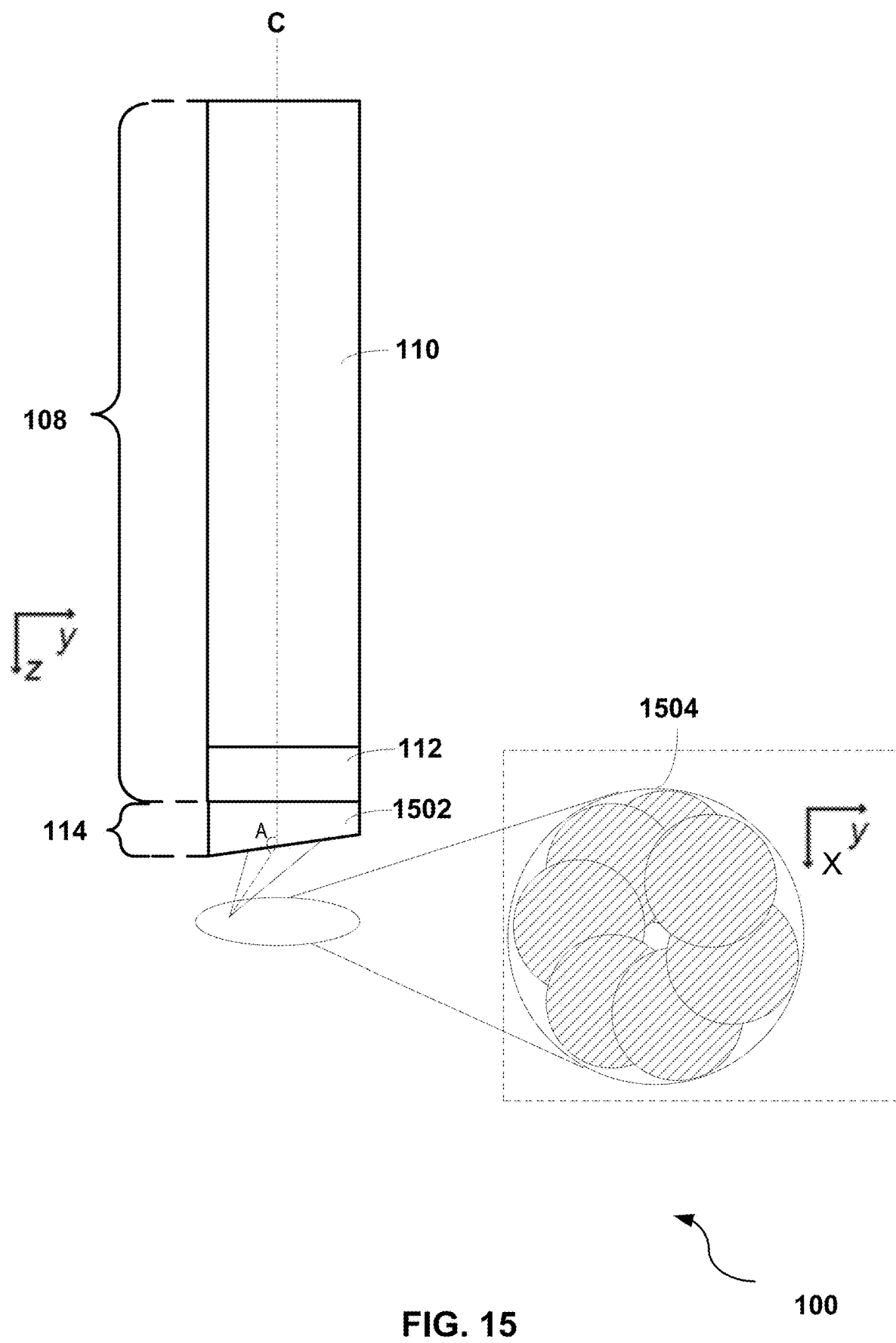
FIG. 15 illustrates an eight example of an optical tissue imaging system.

FIG. 15 illustrates an eighth example of the system. In some examples, the system may provide a large field of view imaging through the distal end of the probe 102. For example, the mirror may include with a wedge prism 1502 to tilt the image angle A. Thus, light may travel through the lens configuration, through the wedge prism, and out the distal end of the probe at the angle A. Unlike conventional approaches where viewing is restricted to the optical axis, the probe provides a significantly larger field of view through rotation of the wedge prism 1502.

The logic illustrated in the flow diagrams may include additional, different, or fewer operations than illustrated. The operations illustrated may be performed in an order different than illustrated. The system 100 may be implemented with additional, different, or fewer components than illustrated. Each component may include additional, different, or fewer components.

Figure 16:
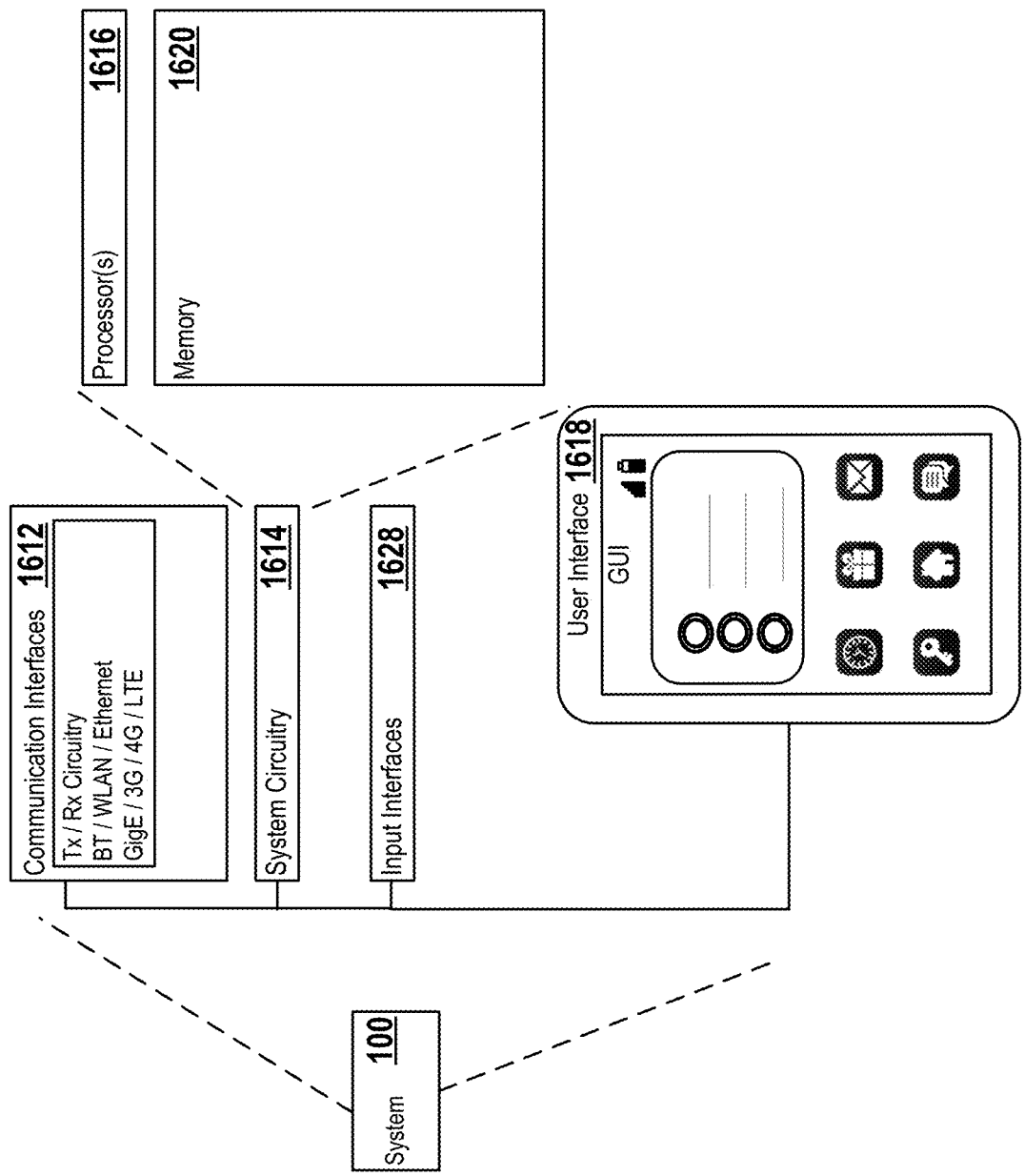
FIG. 16 illustrates a ninth example of a system.

FIG. 16 illustrates a ninth example of the system 100. The system 100 may include communication interfaces 1612, input interfaces 1628 and/or system circuitry 1614. The system circuitry 1614 may include a processor 1616 or multiple processors. Alternatively or in addition, the system circuitry 1614 may include memory 1620.

The processor 1616 may be in communication with the memory 1620. In some examples, the processor 1616 may also be in communication with additional elements, such as the communication interfaces 1612, the input interfaces 1628, and/or the user interface 1618. Examples of the processor 1616 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 1616 may be one or more devices operable to execute logic. The logic may include computer executable instructions or computer code stored in the memory 1620 or in other memory that when executed by the processor 1616, cause the processor 1616 to perform the operations the system 100. The computer code may include instructions executable with the processor 1616.

The memory 1620 may be any device for storing and retrieving data or any combination thereof. The memory 1620 may include non-volatile and/or volatile memory, such as a random access memory (RAM), a read-only memory (ROM), an erasable programmable read-only memory (EPROM), or flash memory. Alternatively or in addition, the memory 1620 may include an optical, magnetic (hard-drive), solid-state drive or any other form of data storage device. Alternatively or in addition, the memory may include any other component or sub-component of the system 100 described herein.

The user interface 1618 may include any interface for displaying graphical information. The system circuitry 1614 and/or the communications interface(s) 1612 may communicate signals or commands to the user interface 1618 that cause the user interface to display graphical information. Alternatively or in addition, the user interface 1618 may be remote to the system 100 and the system circuitry 1614 and/or communication interface(s) may communicate instructions, such as HTML, to the user interface to cause the user interface to display, compile, and/or render information content. In some examples, the content displayed by the user interface 1618 may be interactive or responsive to user input. For example, the user interface 1618 may communicate signals, messages, and/or information back to the communications interface 1612 or system circuitry 1614.

The system 100 may be implemented in many ways. In some examples, the system 100 may be implemented with one or more logical components. For example, the logical components of the system 100 may be hardware or a combination of hardware and software. The logical components may include any component or subcomponent of the system 100. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 1620, for example, that comprises instructions executable with the processor 1616 or other processor to implement one or more of the features of the logical components. When any one of the logical components includes the portion of the memory that comprises instructions executable with the processor 1616, the component may or may not include the processor 1616. In some examples, each logical component may just be the portion of the memory 1620 or other physical memory that comprises instructions executable with the processor 1616, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL)).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks, flash memory drives, floppy disks, and CD-ROMs. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory.

Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. An optical tissue imaging system comprising:
    a transparent cylindrical capillary for insertion into a brain tissue, the transparent cylindrical capillary having an internal cylindrical channel that extends along a central axis of the transparent cylindrical capillary; and
    a probe comprising a mirror configured to reflect light to the brain tissue adjacent to a cylindrical wall of the transparent cylindrical capillary, the probe being rotatable within the transparent cylindrical capillary and movable along the central axis of the transparent cylindrical capillary;
    wherein the mirror is positioned at a first end of the probe,
    wherein the mirror is configured to reflect light received at a second end of the probe to the brain tissue, and
    wherein the mirror is configured to direct light reflected or emitted from the brain tissue to the second end of the probe.

2. The optical tissue imaging system of claim 1, wherein the mirror comprises a folding mirror or prism.

3. The optical tissue imaging system of claim 1, wherein the mirror comprises an aspherical reflection surface,
    wherein the internal cylindrical channel is filled with air without liquid.

4. The optical tissue imaging system of claim 1, further comprising:
    a light sensor configured to generate an optical signal representative of an intensity of the light reflected from the mirror.

5. The optical tissue imaging system of claim 4, wherein the light sensor comprises a photomultiplier tube (PMT).

6. The optical tissue imaging system of claim 1, further comprising a camera configured to receive the light from the mirror and generate wide field images of the brain tissue surrounding the transparent cylindrical capillary as the probe is rotated and moved along the central axis of the transparent cylindrical capillary.

7. The optical tissue imaging system of claim 1, wherein the mirror reflects the light at an angle between 30 and 150 degrees relative to the central axis of the transparent cylindrical capillary.

8. The optical tissue imaging system of claim 1, further comprising a rotary stage configured to selectively rotate the probe in the internal cylindrical channel of the transparent cylindrical capillary.

9. The optical tissue imaging system of claim 1, wherein the probe further comprises a gradient index lens.

10. The optical tissue imaging system of claim 1, wherein the probe further comprises a relay lens and an objective lens positioned in between the relay lens and mirror.

11. The optical tissue imaging system of claim 1, wherein the transparent cylindrical capillary comprises a first capillary, where in the probe further comprises:
    a second capillary; and
    a micromotor,
    where in the micromotor and mirror are disposed inside of the second capillary and the micromotor is bonded to the mirror and second capillary, wherein the micromotor is configured to rotate the mirror in the second capillary.

12. A method, comprising:
    inserting a transparent cylindrical capillary into a brain tissue of a mammal;
    attaching a probe to a rotary stage;
    positioning the probe in line of sight of a camera;
    spinning the probe;
    capturing images of the probe in a plurality of positions specified by the spinning;
    identifying a rotational axis of the rotary stage based on the images;
    aligning the probe with the rotational axis;
    inserting the probe into an opening of the transparent cylindrical capillary, the probe comprising a mirror;
    emitting a light through the probe and onto the mirror to cause the light to be directed onto the brain tissue located radially outward from the transparent cylindrical capillary;
    rotating the mirror;
    translating the mirror axially along the transparent cylindrical capillary; and
    capturing light reflected or emitted onto the mirror from the brain tissue at various locations specified by the rotating and translating.

13. The method of claim 12, wherein before inserting the transparent cylindrical capillary into the brain tissue of the mammal, the method further comprising:
    positioning the opening of the transparent cylindrical capillary in line of sight of a first camera; and
    based on images provided by the camera, move at least a portion of the mammal to align a central axis of the transparent cylindrical capillary with a viewing axis of the first camera, the viewing axis previously calibrated to be parallel with a rotational axis of a rotary stage detachable coupled to the probe.

14. The method of claim 13, further comprising:
    translating the transparent cylindrical capillary to the rotational axis of a rotary stage configured to rotate the probe.

15. The method of claim 13, further comprising:
calibrating the first camera before insertion of the transparent cylindrical capillary into the mammal by:
aligning the transparent cylindrical capillary with a rotational axis of the probe;
translating the transparent cylindrical capillary to a position in line of sight of the first camera; and
adjusting the first camera to align the viewing axis of the first camera with the central axis of the transparent cylindrical capillary.

16. The method of claim 12, wherein the camera comprises a first camera and a second camera, the line of sight of the first camera being substantially orthogonal to the line of sight of the second camera.

17. The method of claim 12, wherein identifying a rotational axis of the rotary stage based on the images further comprises:
identifying, based on the images, corresponding edges of the probe in a plurality of positions; and
determining the rotational axis of the rotary stage based the identified corresponding edges in the plurality of positions.

18. An optical tissue imaging system comprising:
a transparent cylindrical capillary for insertion into a brain tissue, the transparent cylindrical capillary having an internal cylindrical channel that extends along a central axis of the transparent cylindrical capillary; and
a probe comprising a mirror configured to reflect light to the brain tissue adjacent to a cylindrical wall of the transparent cylindrical capillary, the probe being rotatable within the transparent cylindrical capillary and movable along the central axis of the transparent cylindrical capillary;
wherein the mirror reflects the light at an angle between 30 and 150 degrees relative to the central axis of the transparent cylindrical capillary.

19. An optical tissue imaging system comprising:
a transparent cylindrical capillary for insertion into a brain tissue, the transparent cylindrical capillary having an internal cylindrical channel that extends along a central axis of the transparent cylindrical capillary; and
a probe comprising a mirror configured to reflect light to the brain tissue adjacent to a cylindrical wall of the transparent cylindrical capillary, the probe being rotatable within the transparent cylindrical capillary and movable along the central axis of the transparent cylindrical capillary;
wherein the mirror is positioned at a first end of the probe, the probe further comprising a relay lens and an objective lens positioned in between the relay lens and mirror.

20. The optical tissue imaging system of claim 19, further comprising a camera configured to receive the flight from the mirror and generate wide field images of the brain tissue surrounding the transparent cylindrical capillary as the probe is rotated and moved along the central axis of the transparent cylindrical capillary.

* * * * *